(12) United States Patent
Almario et al.

(10) Patent No.: US 9,408,419 B2
(45) Date of Patent: Aug. 9, 2016

(54) MOISTURIZING FABRIC MATERIAL, USE THEREOF IN MOISTURIZING BRAS, AND METHOD OF MANUFACTURE

(75) Inventors: Dulce Almario, Jersey City, NJ (US); Mark Knitowski, Hillsborough, NJ (US); Nathalie Martinet, Hong Kong (CN); Robert J. Smith, Columbus, OH (US); Mayur Vansia, Wayne, NJ (US); Jasmine Yip, Hong Kong (CN)

(73) Assignee: Victoria's Secret Store Brand Management, Inc., Reynoldsburg, OH (US)

( * ) Notice: Subject to any disclaimer, the term of this patent is extended or adjusted under 35 U.S.C. 154(b) by 688 days.

(21) Appl. No.: 13/428,563

(22) Filed: Mar. 23, 2012

(65) Prior Publication Data

US 2013/0252511 A1   Sep. 26, 2013

(51) Int. Cl.

| | |
|---|---|
| A61K 9/70 | (2006.01) |
| A61K 36/63 | (2006.01) |
| A41C 3/00 | (2006.01) |
| A61K 8/73 | (2006.01) |
| D06M 13/02 | (2006.01) |
| D06M 13/224 | (2006.01) |
| D06M 15/03 | (2006.01) |
| D06M 16/00 | (2006.01) |
| A61Q 19/00 | (2006.01) |
| A61K 8/92 | (2006.01) |

(Continued)

(52) U.S. Cl.
CPC .............. *A41C 3/0042* (2013.01); *A61K 8/0208* (2013.01); *A61K 8/738* (2013.01); *A61K 8/922* (2013.01); *A61K 8/97* (2013.01); *A61Q 19/00* (2013.01); *D06M 13/02* (2013.01); *D06M 13/224* (2013.01); *D06M 13/2243* (2013.01); *D06M 15/03* (2013.01); *D06M 16/00* (2013.01)

(58) Field of Classification Search
CPC ........ A61K 36/00; A61K 36/63; A61K 36/899
USPC .......................................... 424/725, 750, 777
See application file for complete search history.

(56) References Cited

U.S. PATENT DOCUMENTS

| | | |
|---|---|---|
| 4,201,822 A | 5/1980 | Cowsar |
| 4,357,468 A | 11/1982 | Szejtli et al. |

(Continued)

FOREIGN PATENT DOCUMENTS

| | | |
|---|---|---|
| CN | 102041678 | 5/2011 |
| CN | 202559161 | 11/2012 |

(Continued)

OTHER PUBLICATIONS

European Search Report for EP13160317.7 dated Oct. 24, 2013.

(Continued)

*Primary Examiner* — Chris R Tate
*Assistant Examiner* — Deborah Davis
(74) *Attorney, Agent, or Firm* — Andrus Intellectual Property Law, LLP

(57) ABSTRACT

Disclosed are moisturizing fabric materials for use in articles of wear such as bras. The moisturizing fabric materials include a moisturizer comprising plant oil, plant extract, and an emulsifier. The moisturizer is bonded to polymeric fabric material via a bonding agent to provide the moisturizing fabric material. Also disclosed is a method of manufacturing an article of wear such as a bra using moisturizing fabric material.

12 Claims, 3 Drawing Sheets

(51) Int. Cl.
*A61K 8/97* (2006.01)
*A61K 8/02* (2006.01)

(56) References Cited

U.S. PATENT DOCUMENTS

| | | | |
|---|---|---|---|
| 4,361,617 A | 11/1982 | Suzuki et al. | |
| 4,391,872 A | 7/1983 | Suzuki et al. | |
| 4,485,058 A | 11/1984 | Suzuki et al. | |
| 4,535,152 A | 8/1985 | Szejtli et al. | |
| 4,774,329 A | 9/1988 | Friedman | |
| 4,822,220 A | 4/1989 | Danielsson et al. | |
| 5,232,769 A * | 8/1993 | Yamato et al. | 442/123 |
| 5,407,609 A | 4/1995 | Tice et al. | |
| 5,608,015 A | 3/1997 | Yoshinaga | |
| 5,776,842 A | 7/1998 | Wood et al. | |
| 5,855,655 A | 1/1999 | Nohr et al. | |
| 5,882,565 A | 3/1999 | Wood et al. | |
| 5,904,936 A | 5/1999 | Huille et al. | |
| 6,190,699 B1 | 2/2001 | Luzzi et al. | |
| 6,287,581 B1 | 9/2001 | Krzysik et al. | |
| 6,391,946 B2 | 5/2002 | Wood et al. | |
| 6,428,814 B1 | 8/2002 | Bosch et al. | |
| 6,440,437 B1 | 8/2002 | Krzysik et al. | |
| 6,475,197 B1 | 11/2002 | Krzysik et al. | |
| 6,485,756 B1 | 11/2002 | Aust et al. | |
| 6,534,074 B2 | 3/2003 | Krzysik et al. | |
| 6,599,627 B2 | 7/2003 | Yeo et al. | |
| 6,607,994 B2 | 8/2003 | Linford et al. | |
| 6,616,869 B2 | 9/2003 | Mathiowitz et al. | |
| 6,616,923 B1 | 9/2003 | Chiou et al. | |
| 6,620,777 B2 | 9/2003 | Heibel et al. | |
| 6,645,525 B1 | 11/2003 | Woiszwillo | |
| 6,677,256 B1 | 1/2004 | Li et al. | |
| 6,746,635 B2 | 6/2004 | Mathiowitz et al. | |
| 6,767,850 B1 | 7/2004 | Tebbe | |
| 6,777,240 B2 | 8/2004 | Hazen et al. | |
| 6,824,791 B2 | 11/2004 | Mathiowitz et al. | |
| 6,849,271 B2 | 2/2005 | Vaghefi et al. | |
| 6,851,461 B2 | 2/2005 | McNicol et al. | |
| 6,861,064 B1 | 3/2005 | Laakso et al. | |
| 6,891,079 B2 | 5/2005 | Koenig et al. | |
| 6,897,168 B2 | 5/2005 | Branham et al. | |
| 6,953,483 B2 | 10/2005 | Litke et al. | |
| 7,154,018 B2 | 12/2006 | Koenig et al. | |
| 7,408,057 B2 | 8/2008 | Renn et al. | |
| 7,455,863 B2 | 11/2008 | Hamann | |
| 7,485,110 B2 | 2/2009 | Koenig et al. | |
| 7,585,526 B2 | 9/2009 | Hamann | |
| 7,776,368 B2 | 8/2010 | Hamann | |
| 2004/0115233 A1 * | 6/2004 | Fukumoto et al. | 424/401 |
| 2004/0120918 A1 | 6/2004 | Lintner et al. | |
| 2007/0077860 A1 | 4/2007 | Brooks | |
| 2007/0190896 A1 * | 8/2007 | Yu | 450/39 |
| 2008/0128941 A1 | 6/2008 | Lopez et al. | |

FOREIGN PATENT DOCUMENTS

| | | |
|---|---|---|
| CN | 103451824 | 12/2013 |
| EP | 0955043 | 11/1999 |
| EP | 1923423 | 5/2008 |
| EP | 1564242 | 4/2010 |
| EP | 2208817 | 7/2010 |
| FR | 2854897 | 11/2004 |
| WO | 2004101609 | 11/2004 |
| WO | 2008035826 | 3/2008 |
| WO | WO 2008035826 A1 * | 3/2008 |

OTHER PUBLICATIONS

"New Heights for Knits", WSA Jul./Aug. 2012, p. 23.
Novarel Brochure, http://www.nurel.com/saludBellezaFirming.do, Jun. 11, 2014.
Bhaskara-Amrit et al., "Applications of beta-Cyclodextrins in Textiles," AUTEX Research Journal, Dec. 2011, 11(4):94.
Examination Report for EP131603171 dated Mar. 7, 2016.
Notice of Allowance issued for CA2,794,775 dated Jan. 26, 2016.
Examination Report for CA2794775 dated Aug. 14, 2015.

* cited by examiner

MOISTURIZING FABRIC MATERIAL, USE THEREOF IN MOISTURIZING BRAS, AND METHOD OF MANUFACTURE

FIELD

The present disclosure relates to the field of women's lingerie, namely bras. Specifically, the present disclosure relates to bras that moisturize a user's skin.

BACKGROUND

When fixing a moisturizer to a fabric, several factors need to be taken into account. If the moisturizer is not fixed to the fabric chemically, the moisturizer may wash out of the clothing with one or more washings. The moisturizer and the chemical used to bond the moisturizer to the fabric may cause the fabric to turn yellow, resulting in unpleasing aesthetics. Further, specifically when molding a bra, it is important to control the temperature of the fabric to ensure proper bonding between the chemical, moisturizer, and fabric.

SUMMARY

The present disclosure relates to moisturizers, moisturizing fabric material and use of the moisturizing fabric material in articles of wear such as bras. The present disclosure also relates to methods of manufacturing the disclosed moisturizing fabric material and articles of use containing the moisturizing fabric material such as bras.

The disclosed moisturizing fabric material includes a moisturizer which typically includes: (a) one or more plants oils and/or one or more plant extracts, and (b) one or more emulsifiers. The moisturizer may be formulated as a moisturizing formula that includes the moisturizer and a bonding agent for bonding the moisturizer to a fabric material.

The disclosed moisturizing fabric material may be utilized in a moisturizing bra cup comprising a cupped inner half having a first fabric lining and cupped outer half having a second fabric lining. The moisturizing formula may be applied to the first fabric lining of the cupped inner half of the moisturizing bra cup. The bonding agent of the moisturizing formula bonds the moisturizer to the fabric of the first lining. The first lining typically is positioned for contact with the user's skin to thereby release moisturizer to the user's skin. Moisturizer that is not released to the user's skin is retained on the fabric of the first lining by the bonding agent for subsequent washing and wear.

A method for forming a moisturizing bra cup is also disclosed. The method comprises treating a first fabric liner with a moisturizing formula comprising a moisturizer and a bonding agent. The method also includes molding a first layer of foam between a first sealing film and the treated first fabric liner to create an inner cupped half of the bra cup. The method further includes molding a second layer of foam between a second sealing film and the second fabric liner to create an outer cupped half of the bra cup. The inner cupped half and outer cupped half are then molded together. Molding of the inner cupped half fixes the bonding agent to the fabric of the first liner.

DETAILED DESCRIPTION

Figure 1:
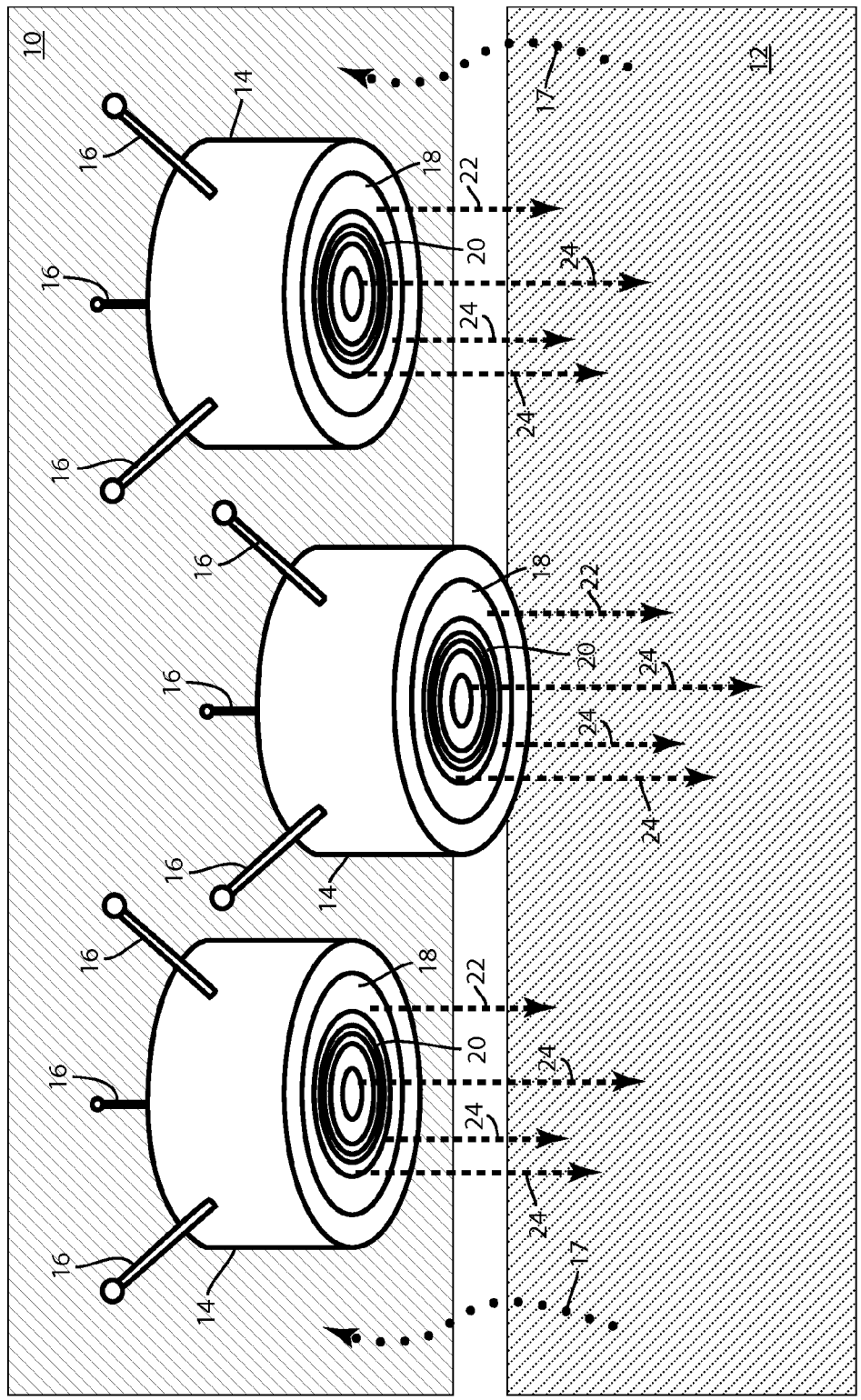
FIG. 1 is a schematic of the bonding agent and moisturizer of the present disclosure.

The present invention is described herein using several definitions, as set forth below and throughout the application.

Unless otherwise specified or indicated by context, the terms "a", "an", and "the" mean "one or more." For example, "a moisturizer" should be interpreted to mean "one or more moisturizers." Similarly, "a bonding agent" should be interpreted to mean "one or more bonding agents."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." For example, a "moisturizing formula that includes a moisturizer" should be interpreted to mean "a moisturizing formula that comprises a moisturizer."

The presently disclosed moisturizers include a plant oil or a plant extract. Suitable plant oils for the disclosed moisturizers may include, but are not limited to, vegetable oils, nut oils, grain oils, or mixtures thereof. Suitable plant oils may include, but are not limited to, olive oil, corn oil, almond oil, apricot oil, coconut oil, avocado oil, hazelnut oil, mongongo nut oil, wheat germ oil, and jojoba oil. Suitable plant oils may include vegetable butters which may include, but are not limited to, cocoa butter and shea butter.

The presently disclosed moisturizers also may include a plant extract, and preferably a plant extract that moisturizes the upper layers of the epidermis. The plant extract may be prepared by extracting plant material with a solvent such as an alcohol (e.g., methanol, ethanol, or propanol) or an ester (e.g., ethyl acetate). The plant extracts may include phytosterols, triglycerides (e.g., caprylic/capric triglyceride), hydrocarbons and branched esters, ceramides and other phytosphingolipids. In some embodiments, the plant extract comprises about 40% hydrocarbons and branched esters, about 30% triglycerides, about 20% phytosterols, and about 10% ceramides and other phytosphingolipids. Suitable plant extracts may be prepared from plant material obtained from one or more plants, including, but not limited to vegetable plants, grain plants, nut plants, and herb plants. Suitable plant material for preparing plant extracts may be obtained from plants including, but not limited to, barley (e.g., where the plant extract comprises hordenine and N,N-dimethyltyramine/4-(2-dimethylamineoethyl)phenol)), tomato (e.g., where the plant extract comprises lycopene), *Salicornia herbacea* (e.g., where the plant extract comprises tungtungmadic acid (3-caffeoyl-4-dihydrocaffeoyl quinic acid), a chlorogenic acid derivative); quercetin 3-O-glucoside/ quercetin 3-O-β-D-glucopyranoside; and isorhamnetin 3-O-glucoside/isorhamnetin 3-O-β-D-glucopyranoside), olive, burdock, licorice, mallow, marsh horsetail, avocado, wheat, soy bean, oat, corn, cotton, millet, coconut, chamomile, aloe, jojoba, thyme, rosemary, spirulina, ginseng, algae, cucumber, hibiscus, pea, almond, shea nut, cocoa (e.g., cocoa nut), grape (e.g., grape seed), and mixtures thereof. Moisturizers comprising plant extracts are disclosed in U.S. Pat. No. 5,800,818, the content of which is incorporated herein by reference in its entirety. Suitable plant extracts may include plant extracts sold under the brand names BMX™ Complex and SALIPORINE-8™ (Barnet Products Corp., Englewood Cliffs, N.J.).

The disclosed moisturizers typically include an emulsifier. Suitable emulsifiers may include, but are not limited to, surfactants including non-ionic surfactants such as silicon-based softeners. Suitable surfactants may include polyethylene glycol compounds such as haloalkyl alcohol substituted polyethylene glycol. Suitable surfactants may include halosurfactants, such as mixtures of haloalkyl alcohol substituted polyethylene glycol with water and a glycol or a glycol ether (e.g., dipropylene glycol methyl ether). Suitable surfactants include fluorosurfactants, such as those sold under the trademarks ZONYL FSN™, ZONYL FSN-100™, ZONYL FSO™, and ZONYL FSO-100™ (Dupont Corp.). Suitable emulsifiers also may include emulsifying waxes (e.g., waxes comprising one or more of the following components: cetearyl alcohol, polysorbates, PEG-150 stearate, and steareth-20), stearyl alcohol, polysorbate 20, polysorbate-40, polysorbate-60, polysorbate 80, lecithin (e.g., soy lecithin), acacia gum, glyceryl stearate, glycol stearate, olive oil PEG 7 esters, sodium stearoyl lactylate, sorbitan oleate, and sorbitan stearate.

The disclosed moisturizers are bonded to a fabric material via a bonding agent. Suitable bonding agents may include cyclodextrin compounds. The use of cyclodextrin compounds as bonding agents for polymeric materials and the synthesis of cyclodextrin compounds are known in the art, e.g., U.S. Pat. Nos. 4,357,468; 4,535,152; 4,774,329; 5,608,015; 5,776,842; 5,855,655; 5,882,565; 6,391,946; 6,677,256; and 6,851,462; the entire contents of which are incorporated herein by reference in their entireties. The cyclodextrin compound may be substituted at one or more hydroxyl positions. Suitable cyclodextrin compounds may include, but are not limited to, acylated cyclodextrin, alkylated cyclodextrin, cyclodextrin esters, hydrocarbyl-amino cyclodextrin, alkyl phosphono cyclodextrin, alkyl phosphato cyclodextrin, imidazolyl substituted cyclodextrin, pyridine substituted cyclodextrin, hydrocarbyl sulfur containing functional groups cyclodextrin, silica-containing functional group substituted cyclodextrin, carbonate substituted cyclodextrin, carboxylic acid substituted cyclodextrin, triazine substituted cyclodextrin, and mixtures thereof. Suitable substituted cyclodextrin compounds may include monochlorotriazinyl-cyclodextrin (e.g., CAS-No. 187820-08-2 sold under the trademark BIOROYAL-1™ (Fukusen Co., Ltd., Wakayama, Japan)).

The disclosed moisturizers may be bonded to a fabric material to provide a moisturizing fabric material. Suitable fabric material may include, but is not limited to, polymeric fabric material having hydroxyl groups (e.g., cellulose material such as cotton), and polymeric fabric material having amino groups or amide groups (e.g., polyamide material such as nylon).

The disclosed moisturizing fabric material may be utilized in articles of wear such as bras as disclosed herein. The disclosed moisturizing fabric material also may be utilized in other articles of use. Articles of use comprising moisturizers are disclosed in U.S. Pat. Nos. 6,287,581; 6,440,437; 6,475,197; 6,485,756; 6,534,074; 6,616,923; 6,777,240; 6,891,079; 7,154,018; 7,408,057; 7,455,863; 7,485,110; 7,585,526; and 7,776,368; the entire contents of which are incorporated herein by reference in their entireties.

FIG. 1 depicts a schematic of the chemical bonding of a moisturizer to a fabric 10 and the release of such moisturizer to a user's skin 12. A bonding agent 14 creates chemical bonds 16 with the fabric 10. The chemical bonds 16 are sufficient to withstand numerous washings of the fabric 10, as described further herein below. This is due to cross linking between the bonding agent 14 and the fabric 10. Preferably, the fabric 10 comprises a material having hydroxyl groups including cellulose fabrics (such as for example, cotton) or amino or amide groups including polyamide materials (such as for example, nylon). For example, the fabric may include nylon 6.

The bonding agent 14 surrounds a moisturizer. The moisturizer contains both oil-based 18 and water-based 20 ingredients. The oil-based 18 ingredients can include, for example, olive oil, SALIPORINE-8™ (Caprylic/Capric Triglyceride and *Salicornia herbacea* Extract, sold by Barnet Products Corp.), and BMX™ Complex (a blend of *Hordeum Vulgare* Extract and *Solanium Lycopersicum* Extract, sold by Barnet Products Corp.). The moisturizer may also contain a surfactant for emulsification. The oil-based ingredients 18 are released from the bonding agent 14 to the user's skin 12 as shown by the arrows 22 in FIG. 1. The water-based ingredients 20 are released from the bonding agent 14 to the user's skin 12 as shown by the arrows 24. Moisturizer not released to the user's skin 12 is retained on the fabric 10 by the bonding agent 14.

The moisturizer is firmly held by the bonding agent 14 due to a strong attachment between the bonding agent 14 and oil even when the fabric 10 is washed or subjected to high temperatures. However, when the fabric 10 comes into contact with a user's skin 12, oils from the user's skin 12 contact the fabric as shown by arrows 17 and pull the moisturizer from the bonding agent 14 to thereby deliver moisturizer to the skin 12. Because the bonding agent 14 is attached to the fabric 10 by molecular bonds 16, it does not wash off despite repeated washes. This is due to the chemical bonds 16 created between the bonding agent 14 and the nylon or cellulose fabric 10 when treated with water and heat. Preferably, the oil-based ingredient 18 is adjacent the bonding agent 14 as shown schematically in FIG. 1, such that the strong bond created between the bonding agent 14 and the oil-based ingredient 18 holds the moisturizer within the bonding agent until it is released to a user's skin 12.

The moisturizer held within the bonding agent 14 preferably comprises olive oil, BMX™ Complex, SALIPORINE-8™, and an emulsifier. The moisturizer may comprise 5% to 50% by weight olive oil, 0.1% to 10% BMX™ complex, 0.1% to 10% SALIPORINE-8™, and 0.1% to 20% emulsifier. The remainder is water. Preferably, the moisturizer comprises 18.8% by weight olive oil, 0.6% BMX™ complex, 0.6% SALIPORINE-8™, and 7% emulsifier, the remainder of which is water.

To treat fabric 10 with the bonding agent 14 and moisturizer, the bonding agent 14 and moisturizer are mixed together with water and a surfactant, such as a silicone-based softener. Preferably, the silicone-based softener is a fluorosurfactant (e.g., the ZONYL™-type fluorosurfactants sold by Dupont Corp.). Together, the bonding agent, moisturizer (comprising oil-based ingredients 18 and water-based ingredients 20), surfactant, and, water create a moisturizing formula into which the fabric 10 is dipped. The moisturizing formula can comprise 0.1% to 10% by weight moisturizer, 0.005% to 1% bonding agent, and 0.1% to 10% fluorosurfactant. Preferably, the moisturizing formula comprises 3% by weight moisturizer, 0.01% bonding agent, and 3% surfactant (as an emulsifier).

The following is an example of a preferred method for creating the moisturizing formula of the present disclosure. Olive oil, BMX™ Complex brand plant extract, and SALIPORINE-8™-type plant extract are mixed together according to the above-described ratios to create the moisturizer (18.8% by weight olive oil, 0.6% BMX™ Complex, 0.6% SALIPORINE-8™, and 7% emulsifier). The moisturizer is added to surfactant, bonding agent, and water such that the moisturizer comprises 3% by weight of the mixture, the surfactant comprises 3% of the mixture, and the bonding agent comprises 0.01% of the mixture. The bonding agent may need to be mixed in warm water prior to being mixed with the other ingredients so that it dissolves adequately. Each of the ingredients (moisturizer, surfactant, and bonding agent) should be mixed with water prior to mixing the three ingredients together to create the moisturizing formula.

Figure 2:
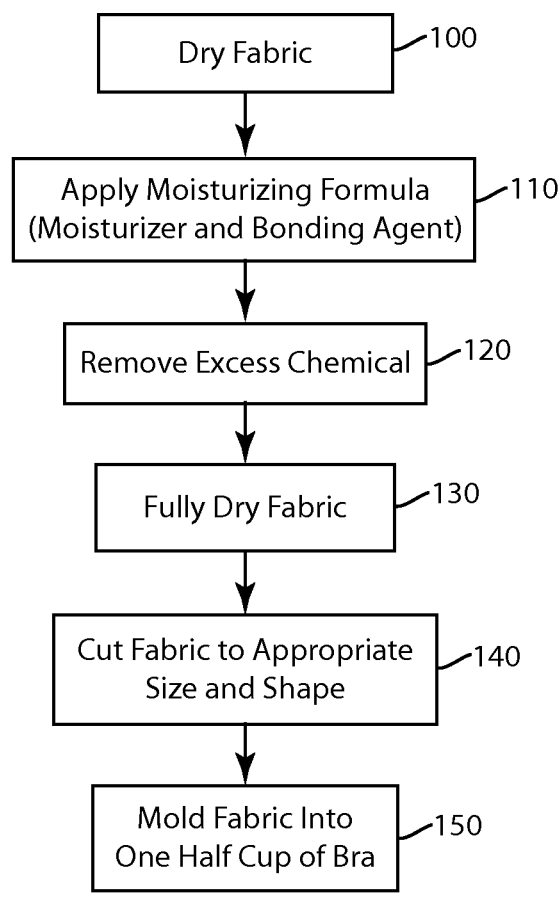
FIG. 2 is a flowchart describing the process used to manufacture the moisturizing bra of the present disclosure.

Now with reference to FIG. 2, a process for treating fabric to be used in a moisturizing bra cup will be described. The fabric 10 is first fully dried after dying, as shown at 100. The fabric is then soaked in the moisturizing formula, comprising the moisturizer, bonding agent and softener, as shown at 110. This process is known as "padding." After padding, the fabric goes through a process at 120 called "mangling", where excess chemical is removed from the fabric by passing it between two squeeze rollers. After mangling, the fabric should preferably weigh at least 1.8 times its original dry weight. Next, the fabric is dried, as shown at 130. The fabric may be dried by a stenter set at a temperature between 80° C.-120° C. The fabric should be fully dried before moving on to the next step. Next, as shown at 140, the fabric is cut to an appropriate size and shape for the bra cup. The fabric is then molded into one half-cup of the bra at 150, as will be described further herein below with reference to FIG. 3.

Figure 3:
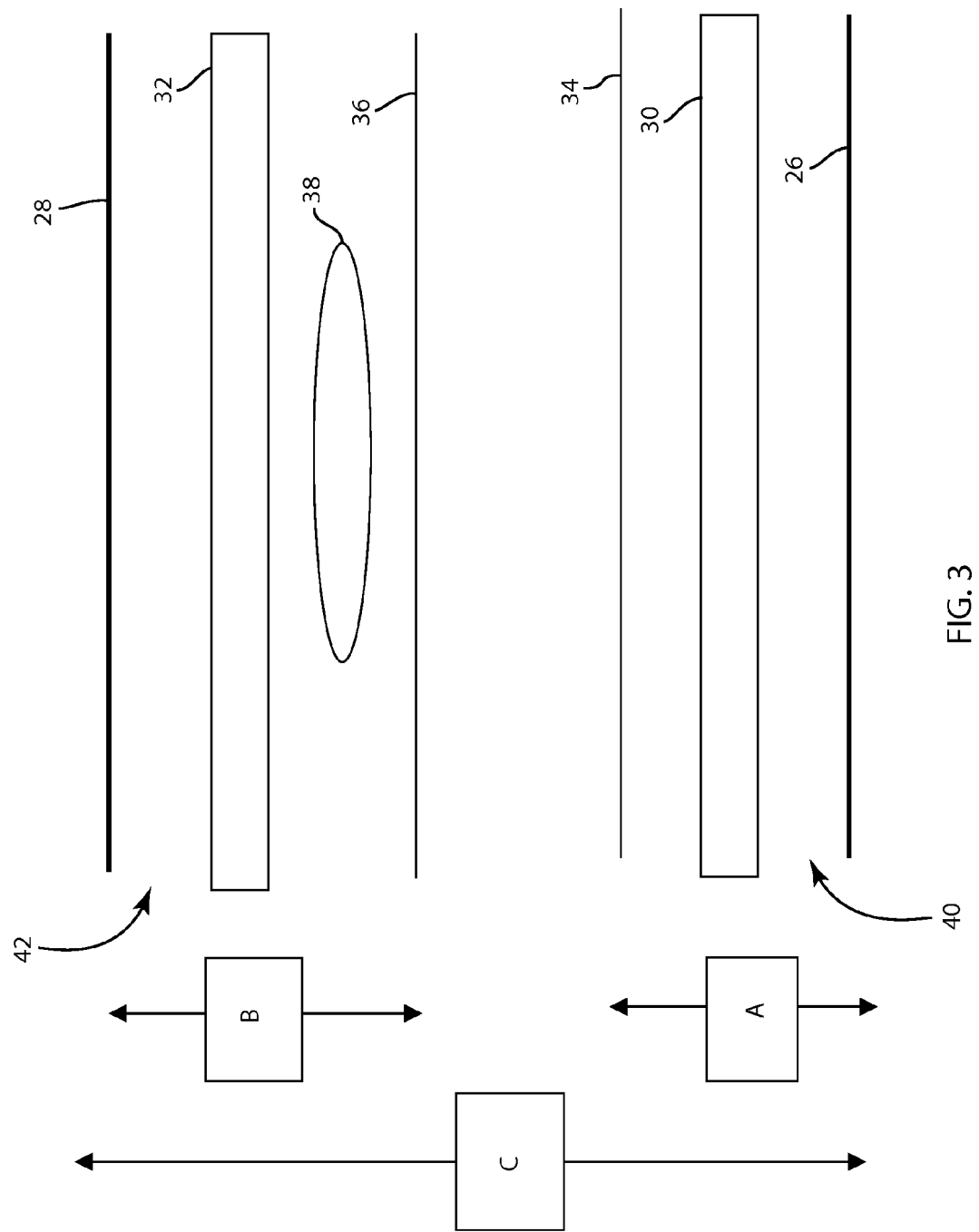
FIG. 3 is a schematic disclosing the structure and method for forming the bra cup halves of the present disclosure.

Now with reference to FIG. 3, a moisturizing bra cup and its method of manufacture will be described. Generally, the moisturizing bra cup comprises a first lining 26, a second lining 28, a first layer of foam 30, a second layer of foam 32, a first sealing film 34, a second sealing film 36, and a layer of shaved foam 38. Together, the first lining 26, first layer of foam 30, and first sealing film 34 comprise an inner cupped half 40 of the moisturizing bra cup. Together, the second lining 28, second layer of foam 32, layer of shaved foam 38, and second sealing film 36 comprise an outer cupped half 42 of the moisturizing bra cup. Preferably, the inner cupped half 40 is positioned on a user such that the first lining 26 contacts the user's skin. The first lining 26 is treated with the moisturizing formula as described herein above. Preferably, the lining 26 is nylon 6.

The molding process is what is known as a "two-step process". This means that each cupped half 40, 42 only undergoes the molding process twice. This ensures that the bonding agent 14 is fixed to the first fabric liner 26, but does not encounter any undesirable side effects such as yellowing or non-adherence of the bonding agent 14 to the fabric 26 after repeated washing.

The first time each cupped half 40, 42 undergoes molding is outlined as follows: To mold the inner cupped half 40 of the moisturizing bra cup, the first lining 26, first layer of foam 30, and first sealing film 34 are molded at a temperature of between 180° C.-195° C. for between 150 to 170 seconds as shown at A. Preferably, the inner cupped half 40 is molded at 190° C. for 160 seconds. This ensures that the bonding agent 14 is fixed to the fabric 10 via chemical bonds 16 (see FIG. 1), because in order for adequate bonding to take place, the fabric 10 must be subjected to temperatures above 180° C. To mold the outer cupped half 42 of the moisturizing bra cup, the second lining 28, second layer of foam 32, layer of shaved foam 38, and second sealing film 36 are molded together as shown at B. Preferably, this takes place at 190° C. for 150 seconds.

The second time that each of the cupped halves 40, 42 undergo molding is at C. At step C, the Inner cupped half 40 and outer cupped half 42 are molded to one another along their respective first sealing film 34 and second sealing film 36. Thus, the first sealing film 34 and the second sealing film 36 are positioned adjacent one another when the inner 40 and outer 42 cupped halves are assembled together. This ensures that the inner 40 and outer 42 cupped halves are molded together such that the first liner 26 is exposed for contact with a user's skin. Preferably, step C takes place at 100° C. for 4 seconds.

The moisturizing bra cup is then assembled into a moisturizing bra according to methods known to those of skill in the art.

The following are test results regarding yellowing of the material, adherence of the moisturizer to fabric after repeated washings, and actual moisturization of a user's skin.

The treated fabric underwent several tests regarding natural weathering, exposure to sunlight, and exposure to air. The formulations described above produced an acceptable level of yellowing in each of the trials.

A fabric treated with 2% olive oil, 0.01% bonding agent, and 5% surfactant, which is similar to the preferred embodiment above, was tested for retention of olive oil on the fabric. The fabric was subjected to repeated washings. After 30 washes, sufficient oil remained on the fabric for subsequent moisturization of a user's skin. When fabric that did not undergo the molding process (i.e., did not achieve temperatures above 180° C. needed for bonding of the bonding agent 14 to the fabric 10) the oil washed off after only 5 washes. In contrast, fabric that had undergone the molding process retained a substantial amount of oil.

Finally, although a clinical trial did not show statistically significant moisturizing effects to a user's skin, a focus study did report favorable results for the moisturizing bra. One user reported a tingling sensation, but this was not seen to be a detriment to the beneficial effect of the moisturizing bra.

In the present description, certain terms have been used for brevity, clearness, and understanding. No unnecessary limitations are to be inferred therefrom beyond the requirement of the prior art because such terms are used for descriptive purposes only and are intended to be broadly construed. The different compositions, manufactures, and methods described herein may be used alone or in combination with other compositions, manufactures, or methods. Various equivalents, alternatives, and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

We claim:

1. A moisturizing fabric comprising a moisturizing formula bonded to a polymeric fabric material, the moisturizing formula comprising a moisturizer and a cyclodextrin compound, the moisturizer comprising:
   (a) about 5% to about 50%, by weight of olive oil; and
   (b) one or more emulsifiers,
wherein the moisturizing fabric is prepared by heating the moisturizing formula and the polymeric fabric material to a temperature above 180° C., wherein the cyclodextrin compound surrounds the moisturizer, cross-links with the polymeric fabric material, and bonds the moisturizer to the polymeric fabric material.

2. The moisturizing fabric material of claim 1, wherein the moisturizer further comprises one or more plant extracts that are prepared from grain material.

3. The moisturizing fabric material of claim 1, wherein the moisturizer further comprises one or more plant extracts that are prepared from vegetable material.

4. The moisturizing fabric material of claim 1, wherein the one or more emulsifiers include a polyethylene glycol compound.

5. The moisturizing fabric material of claim 1, wherein the cyclodextrin compound is a triazinyl substituted cyclodextrin compound.

6. The moisturizing fabric material of claim 5, wherein the triazinyl substituted cyclodextrin compound is monochloro-triazinyl-cyclodextrin.

7. The moisturizing fabric material of claim 1, wherein the polymeric fabric material is cellulose material or polyamide material.

8. A moisturizing bra cup comprising the moisturizing fabric of claim 1.

9. A moisturizing bra cup comprising the moisturizing fabric of claim 1:
  (a) a cupped inner half comprising a first fabric lining; and
  (b) a cupped outer half comprising a second fabric lining;
wherein,
  the first fabric lining comprises the moisturizing fabric of claim 1,
  the first fabric lining is positioned for contact with a user's skin to thereby release moisturizer to the user's skin; and
  the moisturizer not released to the user's skin is retained on the fabric of the first lining by the bonding agent.

10. The moisturizing bra cup of claim 9, further comprising a first sealing film and a first layer of foam, wherein the first layer of foam is positioned between the first lining and the first sealing film.

11. The moisturizing bra cup of claim 10, further comprising a second sealing film and a second layer of foam, wherein the second layer of foam is positioned between the second lining and the second sealing film.

12. The moisturizing bra cup of claim 11, wherein the first sealing film and the second sealing film are positioned adjacent one another when the inner and outer cupped halves are assembled together.

* * * * *